(12) United States Patent
Ostroff

(10) Patent No.: US 7,389,139 B2
(45) Date of Patent: *Jun. 17, 2008

(54) SIMPLIFIED DEFIBRILLATOR OUTPUT CIRCUIT

(75) Inventor: Alan H. Ostroff, San Clemente, CA (US)

(73) Assignee: Cameron Health, Inc., San Clemente, CA (US)

( * ) Notice: Subject to any disclaimer, the term of this patent is extended or adjusted under 35 U.S.C. 154(b) by 228 days.

This patent is subject to a terminal disclaimer.

(21) Appl. No.: 11/224,331

(22) Filed: Sep. 12, 2005

(65) Prior Publication Data

US 2006/0009807 A1 Jan. 12, 2006

Related U.S. Application Data

(63) Continuation of application No. 10/011,957, filed on Nov. 5, 2001, now Pat. No. 6,954,670.

(51) Int. Cl.
*A61N 1/00* (2006.01)
(52) U.S. Cl. .............................. 607/5; 607/4
(58) Field of Classification Search ............... 607/4–5, 607/9, 14

See application file for complete search history.

(56) References Cited

U.S. PATENT DOCUMENTS

| | | |
|---|---|---|
| 3,653,387 A | 4/1972 | Ceier |
| 3,710,374 A | 1/1973 | Kelly |
| 4,191,942 A | 3/1980 | Long |
| 4,223,678 A | 9/1980 | Langer et al. |
| 4,402,322 A | 9/1983 | Duggan |
| 4,407,288 A | 10/1983 | Langer et al. |
| 4,602,637 A | 7/1986 | Elmqvist et al. |
| 4,800,883 A | 1/1989 | Winstrom |
| 4,830,005 A | 5/1989 | Woskow |
| 5,109,842 A | 5/1992 | Adinolfi |
| 5,129,392 A | 7/1992 | Bardy et al. |
| 5,144,946 A | 9/1992 | Weinberg et al. |
| 5,184,616 A | 2/1993 | Weiss |
| 5,331,966 A | 7/1994 | Bennett et al. |
| 5,376,103 A | 12/1994 | Anderson et al. |

(Continued)

FOREIGN PATENT DOCUMENTS

EP 0316616 A2 5/1989

(Continued)

OTHER PUBLICATIONS

Olson, Walter H. et al. "Onset and Stability for Ventricular Tachyarrhythmia Detection in an Implantable Pacer-Cardioverter-Defibrillator," *IEEE* (1987) pp. 167-170.

(Continued)

*Primary Examiner*—Carl Layno
*Assistant Examiner*—Jon-Eric Morales
(74) *Attorney, Agent, or Firm*—Pramudji Wendt & Tran, LLP; Ari Pramudji

(57) ABSTRACT

High side driver circuitry for a defibrillator circuit employs respective capacitors connected to respective gates of silicon controlled rectifiers serving as high side switches. Applying a voltage pulse to a selected capacitor turns on the associated SCR. Positive turn-on of the high side SCRs is insured by inserting a constant current source into the low side activation current path at start-up.

17 Claims, 2 Drawing Sheets

U.S. PATENT DOCUMENTS

| | | | |
|---|---|---|---|
| 5,376,104 | A | 12/1994 | Sakai et al. |
| 5,411,547 | A | 5/1995 | Causey, III |
| 5,413,591 | A | 5/1995 | Knoll |
| 5,431,684 | A | 7/1995 | Archer et al. |
| 5,507,781 | A | 4/1996 | Kroll et al. |
| 5,531,765 | A | 7/1996 | Pless |
| 5,601,607 | A | 2/1997 | Adams |
| 5,645,572 | A | 7/1997 | Kroll et al. |
| 5,658,317 | A | 8/1997 | Haefner et al. |
| 5,674,260 | A | 10/1997 | Weinberg |
| 5,690,683 | A | 11/1997 | Haefner et al. |
| 5,697,953 | A | 12/1997 | Kroll et al. |
| 5,713,926 | A | 2/1998 | Hauser et al. |
| 5,718,242 | A | 2/1998 | McClure et al. |
| 5,766,226 | A | 6/1998 | Pedersen |
| 5,836,976 | A | 11/1998 | Min et al. |
| 5,919,211 | A | 7/1999 | Adams |
| 5,935,154 | A | 8/1999 | Westlund |
| 5,941,904 | A | 8/1999 | Johnston et al. |
| 6,014,586 | A | 1/2000 | Weinberg et al. |
| 6,026,325 | A | 2/2000 | Weinberg et al. |
| 6,058,328 | A | 5/2000 | Levine et al. |
| 6,096,063 | A | 8/2000 | Lopin et al. |
| 6,128,531 | A | 10/2000 | Campbell-Smith |
| 6,144,866 | A | 11/2000 | Miesel et al. |
| 6,169,921 | B1 | 1/2001 | KenKnight et al. |
| 6,185,450 | B1 | 2/2001 | Seguine et al. |
| 6,208,895 | B1 | 3/2001 | Sullivan et al. |
| 6,241,751 | B1 | 6/2001 | Morgan et al. |
| 6,411,844 | B1 | 6/2002 | Kroll et al. |
| 6,647,292 | B1 | 11/2003 | Bardy et al. |
| 6,721,597 | B1 | 4/2004 | Bardy et al. |
| 6,754,528 | B2 | 6/2004 | Bardy et al. |
| 6,778,860 | B2 | 8/2004 | Ostroff et al. |
| 6,788,974 | B2 | 9/2004 | Bardy et al. |
| 6,834,204 | B2 | 12/2004 | Ostroff et al. |
| 6,856,835 | B2 | 2/2005 | Bardy et al. |
| 6,865,417 | B2 | 3/2005 | Rissmann et al. |
| 6,866,044 | B2 | 3/2005 | Bardy et al. |
| 6,927,721 | B2 | 8/2005 | Ostroff et al. |
| 2001/0027330 | A1 | 10/2001 | Sullivan et al. |
| 2002/0035377 | A1 | 3/2002 | Bardy et al. |
| 2002/0035378 | A1 | 3/2002 | Bardy et al. |
| 2002/0035379 | A1 | 3/2002 | Bardy et al. |
| 2002/0035381 | A1 | 3/2002 | Bardy et al. |
| 2002/0042629 | A1 | 4/2002 | Bardy et al. |
| 2002/0042634 | A1 | 4/2002 | Bardy et al. |
| 2002/0049476 | A1 | 4/2002 | Bardy et al. |
| 2002/0052636 | A1 | 5/2002 | Bardy et al. |
| 2002/0072773 | A1 | 6/2002 | Bardy et al. |

FOREIGN PATENT DOCUMENTS

| | | |
|---|---|---|
| EP | 0347353 A1 | 12/1989 |
| EP | 0518599 A2 | 6/1992 |
| EP | 0518599 B1 | 6/1992 |
| EP | 0536873 B1 | 7/1992 |
| EP | 0641573 A2 | 8/1994 |
| EP | 0641573 A3 | 8/1994 |
| EP | 0917887 A1 | 10/1998 |
| EP | 0923130 A1 | 7/2001 |
| WO | WO 93/19809 A1 | 10/1993 |
| WO | WO 98/25349 A1 | 6/1998 |
| WO | WO 99/03534 A1 | 1/1999 |
| WO | WO 99/37362 A1 | 7/1999 |
| WO | WO 01/56166 A2 | 8/2001 |
| WO | WO 02/22208 A2 | 3/2002 |
| WO | WO 02/22208 A3 | 3/2002 |
| WO | WO 02/24275 A2 | 3/2002 |
| WO | WO 02/24275 A3 | 3/2002 |
| WO | WO 02/068046 A1 | 9/2002 |
| WO | WO 03/018121 A2 | 3/2003 |

OTHER PUBLICATIONS

Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95-123.

Schuder, John C. et al., "Experimental Ventricular Defibrillation with an Automatic and Completely Implanted System," *Trans. Amer. Soc. Artif. Int. Organs*, vol. XVI (1970) pp. 207-212.

Schuder, John C. et al., "Transthoracic Ventricular Defibrillation in the Dog with Truncated and Untruncated Exponential Stimuli," *IEEE Transactions on Bio-Medical Engineering*, vol. BME 18, No. 6, Nov. 1971, pp. 410-415.

Tietze, U. et al., "Halbleiter-Schaltungstechnik," *Springer-Verlag*, Berlin, Germany (1991) pp. 784-786.

Walters, R.A. et al., "Analog to Digital Conversion Techniques in Implantable Devices," *Annual International Conference of the IEEE Engineering in Medicine and Biology Society*, vol. 13, No. 4 (1991) pp. 1674-1676.

SIMPLIFIED DEFIBRILLATOR OUTPUT CIRCUIT

CROSS-REFERENCE TO CO-PENDING AND RELATED APPLICATIONS

This application is a continuation of U.S. application Ser. No. 10/011,957, filed Nov. 5, 2001, now U.S. Pat. No. 6,954,670, the entire disclosure of which is incorporated herein by reference.

The invention of present application may find use in systems such as are disclosed in the U.S. application Ser. No. 09/663,607, filed Sep. 18, 2000 and entitled "SUBCUTANEOUS ONLY IMPLANTABLE CARDIOVERTER-DEFIBRILLATOR AND OPTIONAL PACER," now U.S. Pat. No. 6,721,597; and U.S. application Ser. No. 09/663,606, filed Sep. 18, 2000 and entitled "UNITARY SUBCUTANEOUS ONLY IMPLANTABLE CARDIOVERTER-DEFIBRILLATOR AND OPTIONAL PACER," now U.S. Pat. No. 6,647,292, the disclosures of which are incorporated herein by reference.

Applications related to the foregoing applications include U.S. application Ser. No. 09/940,283, filed Aug. 27, 2001 and entitled "DUCKBILL-SHAPED IMPLANTABLE CARDIOVERTER-DEFIBRILLATOR CANISTER AND METHOD OF USE," now U.S. Pat. No. 7,065,407; U.S. application Ser. No. 09/940,371, filed Aug. 27, 2001 and entitled "CERAMICS AND/OR OTHER MATERIAL INSULATED SHELL FOR ACTIVE AND NON-ACTIVE S-ICD CAN," now U.S. Pat. No. 7,039,465; U.S. application Ser. No. 09/940,468, filed Aug. 27, 2001 and entitled "SUBCUTANEOUS ELECTRODE FOR TRANSTHORACIC CONDUCTION WITH IMPROVED INSTALLATION CHARACTERISTICS," now abandoned; U.S. application Ser. No. 09/941,814, filed Aug. 27, 2001 and entitled 'SUBCUTANEOUS ELECTRODE WITH IMPROVED CONTACT SHAPE FOR TRANSTHORACIC CONDUCTION," now abandoned; U.S. application Ser. No. 09/940,356, filed Aug. 27, 2001 and entitled "SUBCUTANEOUS ELECTRODE FOR TRANSTHORACIC CONDUCTION WITH HIGHLY MANEUVERABLE INSERTION TOOL," now abandoned; U.S. application Ser. No. 09/940,340, filed Aug. 27, 2001 and entitled "SUBCUTANEOUS ELECTRODE FOR TRANSTHORACIC CONDUCTION WITH LOW-PROFILE INSTALLATION APPENDAGE AND METHOD OF DOING SAME," now U.S. Pat. No. 6,937,907; U.S. application Ser. No. 09/940,287, filed Aug. 27, 2001 and entitled "SUBCUTANEOUS ELECTRODE FOR TRANSTHORACIC CONDUCTION WITH INSERTION TOOL," now abandoned; U.S. application Ser. No. 09/940,377, filed Aug. 27, 2001 and entitled "METHOD OF INSERTION AND IMPLANTATION OF IMPLANTABLE CARDIOVERTER-DEFIBRILLATOR CANISTERS," now U.S. Pat. No. 6,866,044; U.S. application Ser. No. 11/219,024, filed Sep. 5, 2005 and entitled "CANISTER DESIGNS FOR IMPLANTABLE CARDIOVERTER-DEFIBRILLATORS;" U.S. application Ser. No. 09/940,373 and entitled 'RADIAN CURVE-SHAPED IMPLANTABLE CARDIOVERTER-DEFIBRILLATOR CANISTER," now U.S. Pat. No. 6,788,974; U.S. application Ser. No. 09/940,273 and entitled "CARDIOVERTER-DEFIBRILLATOR HAVING A FOCUSED SHOCKING AREA AND ORIENTATION THEREOF," now U.S. Pat. No. 7,069,080; U.S. application Ser. No. 09/940,378, filed Aug. 27, 2001 and entitled "ANTI-BRADYCARDIA PACING FOR A SUBCUTANEOUS IMPLANTABLE CARDIOVERTER-DEFIBRILLATOR," now U.S. Pat. No. 7,146,212; and U.S. application Ser. No. 09/940,266, filed Aug. 27, 2001 and entitled "BIPHASIC WAVEFORM FOR ANTI-TACHYCARDIA PACING FOR A SUBCUTANEOUS IMPLANTABLE CARDIOVERTER-DEFIBRILLATOR," now U.S. Pat. No. 6,856,835; the disclosures of which applications are all incorporated herein by reference.

FIELD OF THE INVENTION

The subject invention relates generally to electronic circuitry and finds particular application in defibrillator circuitry.

BACKGROUND OF THE INVENTION

Defibrillation/cardioversion is a technique employed to counter arrhythmic heart conditions including some tachycardias in the atria and/or ventricles. Typically, electrodes are employed to stimulate the heart with electrical impulses or shocks, of a magnitude substantially greater than pulses used in cardiac pacing.

Defibrillation/cardioversion systems include body implantable electrodes that are connected to a hermetically sealed container housing the electronics, battery supply and capacitors. The entire system is referred to as implantable cardioverter/defibrillators (ICDs). The electrodes used in ICDs can be in the form of patches applied directly to epicardial tissue, or, more commonly, are on the distal regions of small cylindrical insulated catheters tat typically enter the subclavian venous system, pass through the superior vena cava and, into one or more endocardial areas of the heart. Such electrode systems are called intravascular or transvenous electrodes. U.S. Pat. Nos. 4,603,705; 4,693,253; 4,944,300; and 5,105,810; the disclosures of which are all incorporated herein by reference, disclose intravascular or transvenous electrodes, employed either alone, in combination with other intravascular or transvenous electrodes, or in combination with an epicardial patch or subcutaneous electrodes. Compliant epicardial defibrillator electrodes are disclosed in U.S. Pat. Nos. 4,567,900 and 5,618,287, the disclosures of which are incorporated herein by reference. A sensing epicardial electrode configuration is disclosed in U.S. Pat. No. 5,476,503, the disclosure of which is incorporated herein by reference.

In addition to epicardial and transvenous electrodes, subcutaneous electrode systems have also been developed. For example, U.S. Pat. Nos. 5,342,407 and 5,603,732, the disclosures of which are incorporated herein by reference, teach the use of a pulse monitor/generator surgically implanted into the abdomen and subcutaneous electrodes implanted in the thorax. This system is far more complicated to use than current ICD systems using transvenous lead systems together with an active canister electrode and therefore it has no practical use. It has in fact never been used because of the surgical difficulty of applying such a device (3 incisions), the impractical abdominal location of the generator and the electrically poor sensing and defibrillation aspects of such a system.

Recent efforts to improve the efficiency of ICDs have led manufacturers to produce ICDs which are small enough to be implanted in the pectoral region. In addition, advances in circuit design have enabled the housing of the ICD to form a subcutaneous electrode. Some examples of ICDs in which the housing of the ICD serves as an optional additional electrode are described in U.S. Pat. Nos. 5,133,353; 5,261,400; 5,620,477; and 5,658,321, the disclosures of which are incorporated herein by reference.

ICDs are now an established therapy for the management of life threatening cardiac rhythm disorders, primarily ventricular fibrillation (V-Fib). ICDs are very effective at treating V-Fib, but are therapies that still require significant surgery.

As ICD therapy becomes more prophylactic in nature and used in progressively less ill individuals, especially children at risk of cardiac arrest, the requirement of ICD therapy to use intravenous catheters and transvenous leads is an impediment to very long term management as most individuals will begin to develop complications related to lead system malfunction sometime in the 5-10 year time frame, often earlier. In addition, chronic transvenous lead systems, their reimplantation and removals, can damage major cardiovascular venous systems and the tricuspid valve, as well as result in life threatening perforations of the great vessels and heart. Consequently, use of transvenous lead systems, despite their many advantages, are not without their chronic patient management limitations in those with life expectancies of >5 years. The problem of lead complications is even greater in children where body growth can substantially alter transvenous lead function and lead to additional cardiovascular problems and revisions. Moreover, transvenous ICD systems also increase cost and require specialized interventional rooms and equipment as well as special skill for insertion. These systems are typically implanted by cardiac electrophysiologists who have had a great deal of extra training.

In addition to the background related to ICD therapy, the present invention requires a brief understanding of a related therapy, the automatic external defibrillator (AED). AEDs employ the use of cutaneous patch electrodes, rather than implantable lead systems, to effect defibrillation under the direction of a bystander user who treats the patient suffering from V-Fib with a portable device containing the necessary electronics and power supply that allows defibrillation. AEDs can be nearly as effective as an ICD for defibrillation if applied to the victim of ventricular fibrillation promptly, i.e., within 2 to 3 minutes of the onset of the ventricular fibrillation.

AED therapy has great appeal as a tool for diminishing the risk of death in public venues such as in air flight. However, an AED must be used by another individual, not the person suffering from the potential fatal rhythm. It is more of a public health tool than a patient-specific tool like an ICD. Because >75% of cardiac arrests occur in the home, and over half occur in the bedroom, patients at risk of cardiac arrest are often alone or asleep and can not be helped in time with an AED. Moreover, its success depends to a reasonable degree on an acceptable level of skill and calm by the bystander user.

What is needed therefore, especially for children and for prophylactic long term use for those at risk of cardiac arrest, is a combination of the two forms of therapy which would provide prompt and near-certain defibrillation, like an ICD, but without the long-term adverse sequelae of a transvenous lead system while simultaneously using most of the simpler and lower cost technology of an AED. What is also needed is a cardioverter/defibrillator that is of simple design and can be comfortably implanted in a patient for many years.

Circuitry for controlling so-called "high side" switches in defibrillator circuitry has exhibited considerable complexity, necessitating use, for example, of transformers, opto-couplers and/or photo voltaic generators. Such complexity is generally undesirable and particularly undesirable in devices intended for implantation within the human body.

SUMMARY

According to one aspect of the invention, high side defibrillator driver circuitry is provided which employs silicon controlled rectifiers serving as high side switches. Applying a control current to a selected gate of one of the high side SCR's turns on that SCR. According to another aspect of the invention, positive turn-on of the high side SCRs is ensured by inserting a constant current source into the low side activation current path at start-up.

DETAILED DESCRIPTION OF ILLUSTRATIVE EMBODIMENTS

Figure 1:
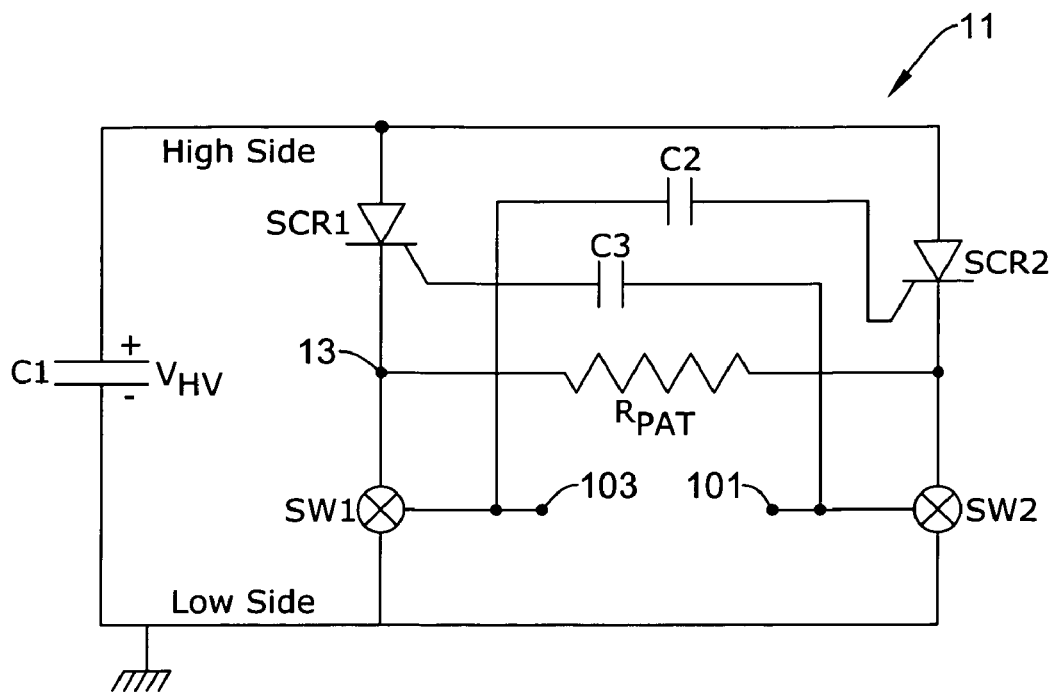
FIG. 1 is an electrical circuit schematic of a circuit according to a first illustrative embodiment of the invention.

FIG. 1 illustrates an electrical circuit including a first illustrative embodiment according to the invention. The circuit includes a high voltage capacitor $C_1$ grounded at one terminal and connected at its opposite terminal to respective anodes of two silicon controlled rectifiers $SCR_1$, $SCR_2$.

The respective cathodes of the respective rectifiers $SCR_1$, $SCR_2$ are connected to respective first terminals of first and second low side switches $SW_1$, $SW_2$. The respective cathodes of the silicon controlled rectifiers $SCR_1$, $SCR_2$ are additionally electrically coupled to respective physical locations on a patient on either side of a patient resistance denoted $R_{PAT}$.

The gate or trigger terminal of the first silicon controlled rectifier $SCR_1$ is connected through a capacitor $C_3$ to a first terminal 101 of the second switch $SW_2$. The gate or trigger terminal of the second silicon controlled rectifier $SCR_2$ is connected through a second capacitor $C_2$ to the first terminal 103 of the first low side switch $SW_1$. Respective second terminals of the switches $SW_1$, $SW_2$ are connected to ground in the embodiment illustrated in FIG. 1.

The respective first terminals 103, 101 of the respective low side switches $SW_1$, $SW_2$ are those which, in response to application of a switching signal, cause the switches $SW_1$, $SW_2$ to close. Hence, the first terminals 101, 103 may comprise, e.g., the gates of respective switching transistors or respective SCRs.

Figure 2:
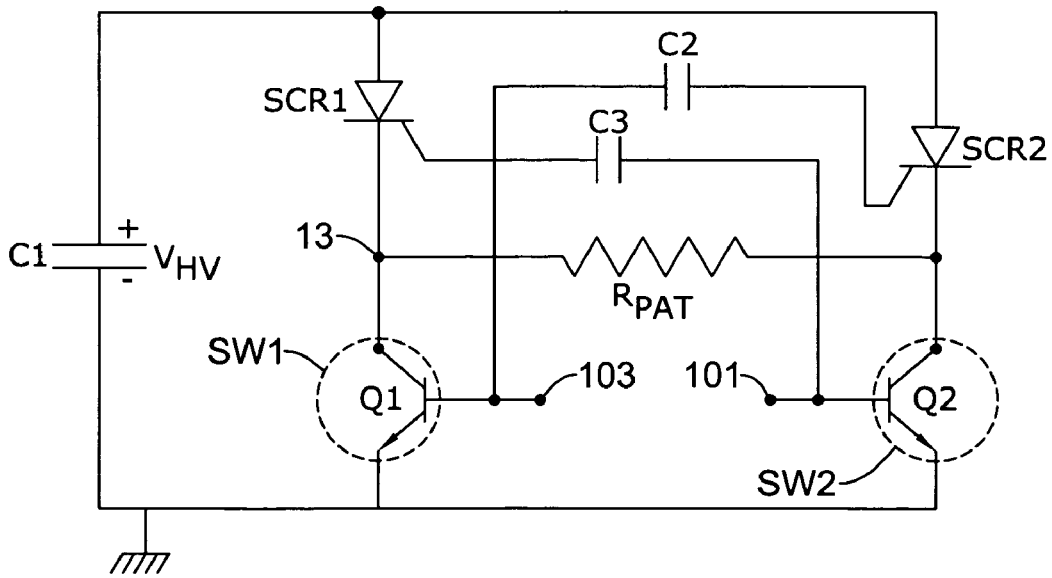
FIG. 2 illustrates the use of low side transistor switches within a circuit like that of FIG. 1.

The embodiment of FIG. 2 particularly illustrates respective transistors $Q_1$, $Q_2$ used as the switching devices in a circuit according to FIG. 1. These transistors may be, for example, IGBTs or MOSFETs. The switches $SW_1$, $SW_2$ can also comprise silicon controlled rectifiers (SCRs).

To illustrate operation of the circuit of FIG. 1, assume a control voltage signal is applied to the first terminal 101 of the second switch $SW_2$. Such application closes the switch $SW_2$ and creates a current through the coupling capacitor $C_3$ into the gate of the first silicon controlled rectifier $SCR_1$, which current turns on $SCR_1$. Activation of the first silicon controlled rectifier $SCR_1$ applies a voltage to the patient resistance $R_{PAT}$ and causes a current to flow through $SCR_1$, $R_{PAT}$, and $SW_2$ to ground. In one application, this current may be terminated by appropriately turning off the switch $SW_2$ to thereby create a monophasic waveform.

To create a biphasic waveform, the switch $SW_2$ is opened for a selected interval, and a control voltage signal is then applied to the first terminal 103 of the first switch $SW_1$. This control voltage signal closes the switch $SW_1$ and creates a drive current into the gate of the second silicon controlled rectifier $SCR_2$, thereby turning $SCR_2$ "on." A current path is thus created from the high voltage capacitor $C_1$ through $SCR_2$, the patient resistance $R_{PAT}$, and the switch $SW_1$, resulting in a negative going pulse, i.e., the second phase of a biphasic waveform.

The circuit of FIG. 1 has a drawback in that it exhibits an extremely rapid change of current with respect to time ("dI/dt"), which may present control problems. Another drawback is that it takes a finite amount of time for the second switch $SW_2$ to come "on," which presents the possibility that the $SCR_1$ will not turn on because a silicon controlled rectifier typically requires a certain amount of current flow through it in order to maintain the "on" state. In such case, the circuit will not switch correctly.

Figure 3:
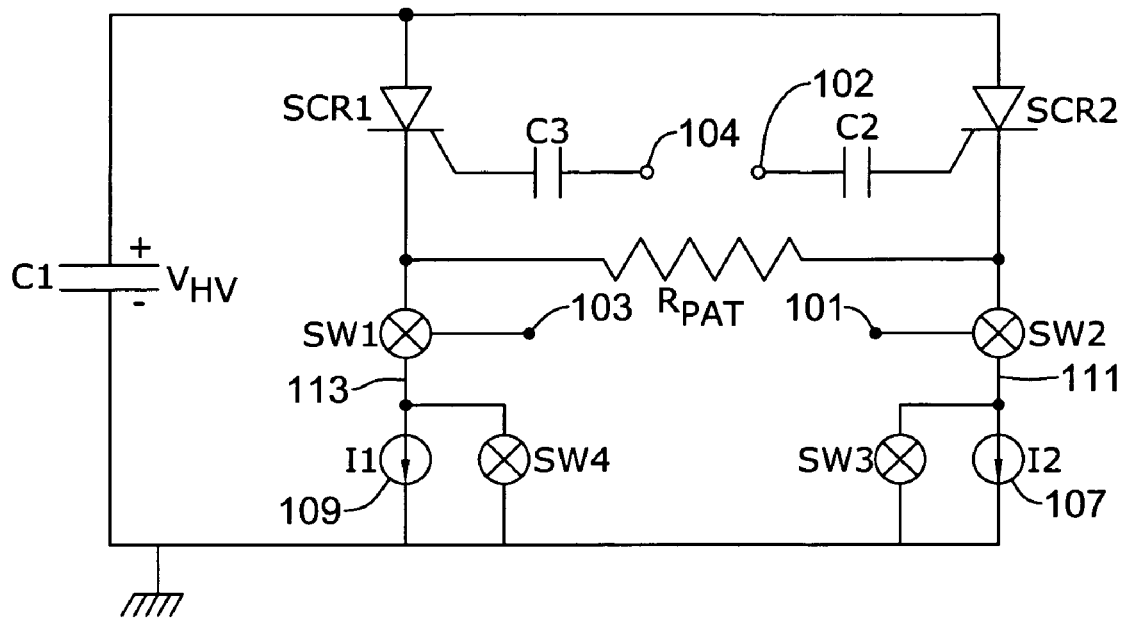
FIG. 3 is an electrical circuit schematic of a second illustrative embodiment.

The embodiment of FIG. 3 improves over those of FIGS. 1 and 2 by providing positive control of switching of the silicon controlled rectifiers $SCR_1$, $SCR_2$ by causing the low side switches $SW_1$, $SW_2$ to operate as current sources.

Thus, in the embodiment of FIG. 3, the capacitors $C_2$, $C_3$ are arranged to have control signals selectively applied to respective terminals 102, 104, which are not connected to the first terminals 101, 103, e.g., gates, of the switching devices $SW_1$, $SW_2$. Additionally, respective constant current source circuits 107, 109 are created in the respective lower legs 111, 113 of the switches $SW_1$, $SW_2$. Third and fourth switches $SW_3$, $SW_4$ are provided to selectively short out the respective constant current sources 107, 109, i.e., create a short circuit around them to ground.

With respect to the operation of the circuit of FIG. 3, various components are selectively activated ("turned on") in order to deliver a monophasic pulse, if desired, or both phases of a biphasic waveform. In order to create a monophasic pulse, for example, the switch $SW_2$ is turned on and enabled to work as a current source. Then the gate of $SCR_1$ is pulsed with a signal applied to the first terminal 104 of the capacitor $C_3$. Once the pulse triggers $SCR_1$, $SCR_1$ is guaranteed to stay on because the current source 107 is activated to supply an amount of current selected to hold $SCR_1$ on.

Figure 4:
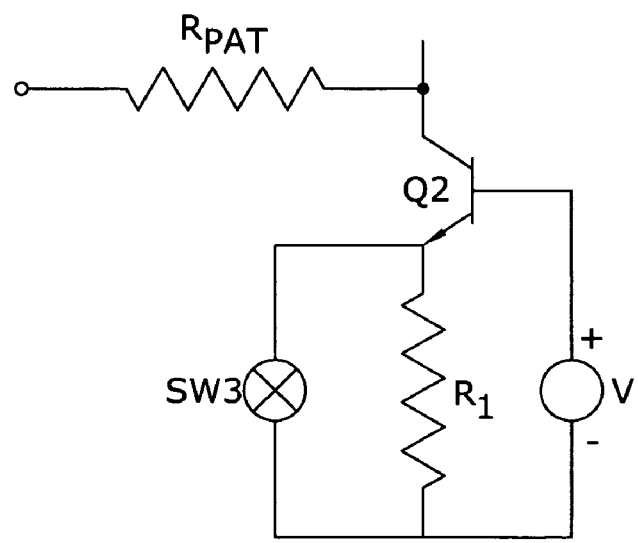
FIG. 4 is an electrical circuit schematic of a current source employable in the circuit of FIG. 3.

An example of a current source circuit 107, 109 is illustrated in FIG. 4, where the transistor $Q_2$ functions as one of the low side switches $SW_1$, $SW_2$ of FIG. 3. The constant voltage V applied across the resistor $R_1$ may be supplied, for example, by a digital to analog converter or other techniques including those shown and described in application Ser. No. 10/011,955, filed Nov. 5, 2001 and entitled Defibrillation Pacing Circuitry, now U.S. Pat. No. 6,952,608, the disclosure of which is incorporated by reference herein.

The current supplied by the current sources 107, 109 can be programmed to any desired amount, e.g., anywhere between 10 to 500 milliamps, but is particularly set to the value of the holding current required by $SCR_1$. Thus, for example, if the holding current is 100 milliamps, the current through $R_{PAT}$ rises from 0 to 100 milliamps very quickly, but only to 100 milliamps. Thus, dI/dt is fairly limited.

At that point (100 ma), the monophase pulse is initiated by turning on the first silicon controlled rectifier $SCR_1$. As soon as $SCR_1$ turns on, the current source 107 is switched out of the circuit, e.g., by creating a short across the resistance $R_1$ of FIG. 4, which results in a very high current ($\cong V_{HV}/R_{PAT}$) with the dI/dt and the dV/dt being controlled by the controlled slew rate of the turn-on and turn-off time of the drive signal. To truncate the monophase pulse, the low side switch $SW_2$ is then turned off, the current goes to 0, and the silicon controlled rectifier $SCR_1$ turns off.

In order to create the second phase of a biphasic waveform, a similar procedure is followed. The switch $SW_1$ is enabled, e.g., by application of a 15 volt pulse with respect to ground, as is the current source $I_1$ in its leg. Then, via the capacitive coupling provided by the capacitor $C_2$, the second silicon controlled rectifier $SCR_2$ is triggered, for example, by application of a 15 volt pulse with respect to ground, but only to the programmed holding current provided via the current source 109. Next, the current source 109 is removed and the current through $R_{PAT}$ ramps up in a controlled manner by controlling the slew rate of the drive signal to create the second phase of the biphasic waveform.

As those skilled in the art will appreciate, the illustrative embodiments employ a high side bridge wherein the drivers each include only two components, the SCRs and the respective capacitors $C_2$, $C_3$. The control voltages applied to the capacitors may range from, for example, 5 to 15 volts. Thus, the high side driver circuitry has been made smaller, simpler, with fewer components. As those skilled in the art appreciate, SCRs are typically smaller devices than IGBTs or MOSFETs, resulting in an even more efficient use of silicon. In addition to these advantages, the dV/dt and the dI/dt are controllable.

While the present invention has been described above in terms of specific embodiments, it is to be understood that the invention is not limited to the disclosed embodiments. On the contrary, the following claims are intended to cover various modifications and equivalent methods and structures included within the spirit and scope of the invention.

What is claimed is:

1. An implantable cardiac stimulus device including circuitry for delivering cardiac stimulus to a patient, the circuitry for delivering cardiac stimulus having a high side for delivering current to a patient and a low side for receiving current from a patient, the circuitry for delivering cardiac stimulus comprising:

a first high side switching device having a control terminal adapted to receive a control current, said control current causing closing of a signal path through said switching device; and a first capacitor coupled to said control terminal and adapted to receive a control voltage selected to create said control current;

wherein said first high side switching device comprises a first silicon controlled rectifier and the circuitry for delivering cardiac stimulus is constructed to include a current source in the low side thereof, the current source being selectively enabled for holding the first silicon controlled rectifier "on" during a selected interval.

2. The implantable cardiac stimulus device of claim 1, wherein the control terminal is the gate of the first silicon controlled rectifier.

3. The implantable cardiac stimulus device of claim 1, wherein the current source includes a first transistor having a resistor coupled thereto, with a switch coupled in parallel with the resistor for selectively shorting signal across the resistor.

4. The implantable cardiac stimulus device of claim 1, wherein the circuitry for delivering cardiac stimulus further includes a second high side switching device having a control terminal adapted to receive a control current, the control current selectively causing closing of a signal path through the second switching device, wherein the second high side switching device is also a silicon controlled rectifier.

5. An H-bridge adapted to provide outputs for use in an implantable cardiac stimulus device, the H-bridge comprising:
a first high side switch having a control terminal;
a second high side switch having a control terminal;
a first low side switch having a control terminal;
a second low side switch having a control terminal;
first and second output nodes for providing an output from the H-bridge, each node being a circuit location in the H-bridge where two of the switches are electrically coupled to one another;
a first capacitor coupling the control terminal of the first high side switch to the control terminal of the first low side switch; and
a second capacitor coupling the control terminal of the second high side switch to the control terminal of the second low side switch;
wherein the first and second high side switches and first and second low side switches are coupled to the first and second nodes such that:
if the first high side switch and first low side switch are simultaneously in a closed state, current is allowed to flow from a high voltage node, through the first high side switch to the first output node and from the second output node through the first low side switch to a low voltage node; and
if the second high side switch and second low side switch are simultaneously in a closed state, current is allowed to flow from the high voltage node, through the second high side switch to the second output node and from the first output node through the second low side switch to the low voltage node.

6. The H-bridge of claim 5, wherein the first and second high side switches are silicon controlled rectifiers, and the control terminals for the first and second high side switches are the respective gates of the silicon rectifiers.

7. The H-bridge of claim 6, wherein the first and second low side switches are IGBTs, and the control terminals for the first and second low side switches are the respective gates of the IGBTs.

8. The H-bridge of claim 5, wherein the first and second low side switches are IGBTs, and the control terminals for the first and second low side switches are the respective gates of the IGBTs.

9. A method of operating an implantable cardiac stimulus device, the implantable cardiac stimulus device comprising at least a first high side switch and a first low side switch configured such that stimulus applied to a patient causes current to flow, in succession,
from a relatively high voltage node through the first high side switch,
through the patient, and
through the first low side switch to a relatively low voltage node,
the implantable cardiac stimulus device further comprising control circuitry having a plurality of outputs for controlling components of the implantable cardiac stimulus device, the method comprising:
applying a first enabling signal generated at a first single output of the control circuitry to each of the first high side switch and the first low side switch; and
providing a circuit path from the first single output of the control circuitry to the first high side switch having first one or more circuit elements that, combined, limit current flow of the first enabling signal to the first high side switch;
wherein the implantable cardiac stimulus device further comprises a second high side switch and a second low side switch, and the first high side switch, the second high side switch, the first low side switch, and the second low side switch are arranged in an H-bridge configuration; and the method further comprises:
applying a second enabling signal generated at a second single output of the control circuitry to each of the second high side switch and the second low side switch; and
providing a circuit path from a second single output of the control circuitry to the second high side switch having second one or more circuit elements that, combined, limit current flow of the second enabling signal to the second high side switch.

10. The method of claim 9, wherein the first one or more circuit elements includes a capacitor.

11. The method of claim 10, wherein the first high side switch is a silicon controlled rectifier.

12. The method of claim 9, wherein the first high side switch is a silicon controlled rectifier.

13. The method of claim 9, wherein the first and second one or more circuit elements each includes a capacitor.

14. The method of claim 13, wherein the first and second high side switches are silicon controlled rectifiers.

15. The method of claim 9, wherein the first and second high side switches are silicon controlled rectifiers.

16. The method of claim 9, further comprising, in association with the first and second enabling signals, providing a high voltage signal coupled to the H-bridge, wherein successive application of the first and second enabling signals causes a biphasic cardiac stimulus waveform to be generated.

17. The method of claim 9, further comprising, in association with the first enabling signal, providing a high voltage signal coupled to the first high side switch, wherein application of the enabling signal causes application of a defibrillation signal to a patient.

* * * * *